United States Patent
Chen et al.

(10) Patent No.: US 10,494,396 B2
(45) Date of Patent: Dec. 3, 2019

(54) METHOD OF SEPARATING BETANIN FROM RED QUINOA BY SUPERCRITICAL FLUID FRACTIONATION

(71) Applicant: National Pingtung University of Science and Technology, Pingtung County (TW)

(72) Inventors: Ho-Hsien Chen, Pingtung County (TW); Chen-Hsing Yu, Pingtung County (TW); Nyvonne Tiqu Gina Nelma, Pingtung County (TW)

(73) Assignee: NATIONAL PINGTUNG UNIVERSITY OF SCIENCE AND TECHNOLOGY, Pingtung County (TW)

(*) Notice: Subject to any disclaimer, the term of this patent is extended or adjusted under 35 U.S.C. 154(b) by 156 days.

(21) Appl. No.: 15/004,099

(22) Filed: Jan. 22, 2016

(65) Prior Publication Data
US 2017/0174717 A1 Jun. 22, 2017

(30) Foreign Application Priority Data
Dec. 17, 2015 (TW) ............................. 104142434 A

(51) Int. Cl.
| C07H 1/08 | (2006.01) |
| C07H 17/02 | (2006.01) |
| C09B 23/16 | (2006.01) |
| C09B 61/00 | (2006.01) |
| C09B 67/54 | (2006.01) |

(52) U.S. Cl.
CPC ............. *C07H 1/08* (2013.01); *C07H 17/02* (2013.01); *C09B 23/164* (2013.01); *C09B 61/00* (2013.01); *C09B 67/0096* (2013.01)

(58) Field of Classification Search
None
See application file for complete search history.

(56) References Cited

U.S. PATENT DOCUMENTS

| 2007/0251024 A1* | 11/2007 | Greaves | A61K 8/97 8/405 |
| 2010/0151098 A1* | 6/2010 | Catchpole | B01D 11/0203 426/425 |

OTHER PUBLICATIONS

Esatbeyoglu, T., Wagner, A. E., Schini-Kerth, V. B., & Rimbach, G. (2015). Betanin—A food colorant with biological activity. Molecular nutrition & food research, 59(1), 36-47.*
Tsai, P. J., Sheu, C. H., Wu, P. H., & Sun, Y. F. (2009). Thermal and pH stability of betacyanin pigment of djulis (Chenopodium formosanum) in Taiwan and their relation to antioxidant activity. Journal of agricultural and food chemistry, 58(2), 1020-1025.*
Betanin chemical and physical properties, website capture of http://foodb.ca/compounds/FDB000497, retrieved on Sep. 13, 2018. (Year: 2018).*
Escribano, J., Cabanes, J., Jiménez-Atiénzar, M., Ibañez-Tremolada, M., Gómez-Pando, L. R., García-Carmona, F., & Gandía-Herrero, F. (2017). Characterization of betalains, saponins and antioxidant power in differently colored quinoa (Chenopodium quinoa) varieties. Food chemistry, 234, 285-294. (Year: 2017).*
Pi-Jen Tsai et al., Effect of nanogrinding on the pigment and bioactivity of Djulis ( Chenopodium formosanum Koidz.), Journal of Agricultural and Food Chemistry, 2011, 59,1814-1820.

* cited by examiner

*Primary Examiner* — Dale R Miller
(74) *Attorney, Agent, or Firm* — Locke Lord LLP; Tim Tingkang Xia, Esq.

(57) ABSTRACT

The present invention relates to a method of separating betanin from red quinoa by supercritical fluid fractionation, including: mixing an extract of red quinoa with an ethanol/water mixture to obtain a mixture of red quinoa/ethanol/water; and separating betanin from the mixture of red quinoa/ethanol/water by supercritical fluid fractionation, which operates under a pressure between 2300 to 4400 psi at a temperature between 35 to 65° C. for a period of time between 15 to 90 minutes.

7 Claims, 1 Drawing Sheet

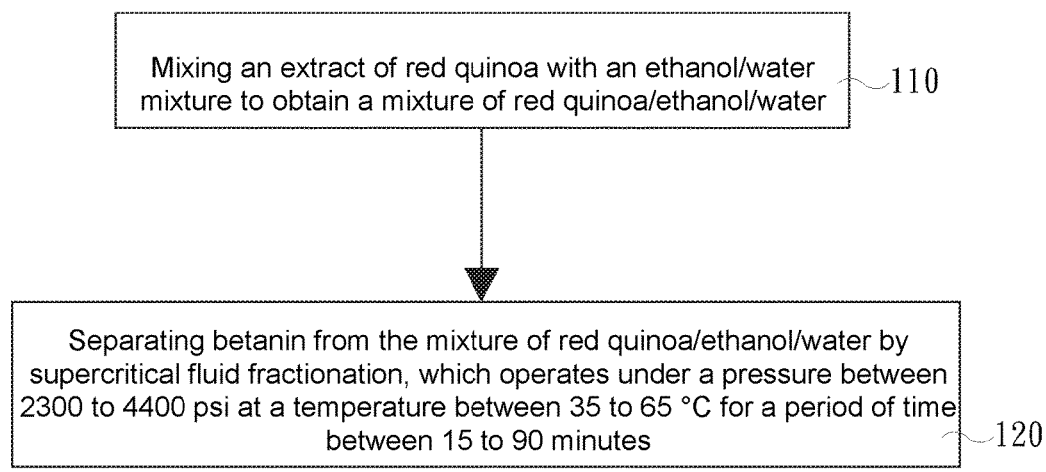

METHOD OF SEPARATING BETANIN FROM RED QUINOA BY SUPERCRITICAL FLUID FRACTIONATION

CROSS REFERENCE

The non-provisional application claims priority from Taiwan Patent Application No. 104142434, filed on Dec. 17, 2015, the content thereof is incorporated by reference herein.

BACKGROUND OF THE INVENTION

Field of the Invention

The present invention relates to a method of separating betanin from red quinoa, and particularly to a method of separating betanin from red quinoa by supercritical fluid fractionation, which increases the content of betanin in the extract of red quinoa effectively.

Description of the Prior Art

Food coloring used in food science and technology is classified into two categories, i.e. natural food dyes and synthetic dyes. In recent years, people concern the safety of synthetic dyes due to frequently reported food safety issues. The natural dyes come directly from animals, plants or microbes. Therefore, the natural dyes are highly safe and non-toxic and have become the main direction of development in food science and technology.

Taiwan quinoa (scientific name: *Chenopodium formosanum*, English name: Red Quinoa) is a native species in Taiwan and traditionally known as red quinoa. Red quinoa is a traditional crop farmed by Taiwanese aboriginals for more than a century. Since the plant body is rich in betalain, the grain thereof has a colorful appearance, including yellow, red, purple, orange and other colors. Red quinoa contains high levels of nutrients, such as protein, starch and dietary fiber. Among them, the red betanin has good antioxidant activity.

Generally, it needs large amount of solvent to extract betanin from red quinoa (betanin:solvent=1:50 to 1:100). As such, the concentration of betanin is not easy and needs complicated procedures.

Therefore, the inventor and related manufacturers engaged in this industry are anxious to study the path of improvement to solve the aforementioned problems and deficiencies.

SUMMARY OF THE INVENTION

In view of the above deficiencies, the inventor of the present invention gathers relevant information through multi-assessment and consideration and finishes the present invention through constantly trials and modifications based on the cumulative experiences in this industry for years.

The object of the present invention is to provide a method of separating betanin from red quinoa by supercritical fluid fractionation, which increases the content of betanin in the extract of red quinoa effectively.

To achieve the above and other objects, the method of separating betanin from red quinoa by supercritical fluid fractionation includes mixing an extract of red quinoa with an ethanol/water mixture to obtain a mixture of red quinoa/ethanol/water; and separating betanin from the mixture of red quinoa/ethanol/water by supercritical fluid fractionation, which operates under a pressure between 2300 to 4400 psi at a temperature between 35 to 65° C. for a period of time between 15 to 90 minutes.

In a preferred embodiment, the ratio of the ethanol/water mixture ranges from 60:40 to 80:20.

In a preferred embodiment, the ratio of the ethanol/water mixture ranges from 60:40 to 70:30.

In a preferred embodiment, the ratio of the ethanol/water mixture is 70:30.

In a preferred embodiment, the pressure is between 2300 to 3700 psi.

In a preferred embodiment, the pressure is 3700 psi.

In a preferred embodiment, the temperature is between 35 to 55° C.

In a preferred embodiment, the temperature is 35° C.

In a preferred embodiment, the period of time is between 30 to 90 minutes.

In a preferred embodiment, the period of time is 30 minutes.

Using the method of separating betanin from red quinoa by supercritical fluid fractionation of the present invention, the content of betanin in the extract of red quinoa is increased from 2400 ppm to 3200 ppm, which equals to a 33% increase. Also, the process for separating betanin of the present invention is unitary and easy to purify.

BRIEF DESCRIPTION OF THE DRAWINGS

FIG. 1 is a flow diagram of a preferred embodiment of the method of separating betanin from red quinoa by supercritical fluid fractionation according to the present invention.

DETAILED DESCRIPTION OF THE EMBODIMENTS

To achieve the above objects and efficacy, the preferred embodiment of the technical means and construction used in the present invention are drawn hereby to illustrate the features and functions as what follows for facilitating fully understanding.

Referring to FIG. 1, which is a flow diagram of a preferred embodiment of the method of separating betanin from red quinoa by supercritical fluid fractionation according to the present invention. It could be seen from the drawing that the method of separating betanin from red quinoa by supercritical fluid fractionation of the present invention included the following steps: mixing an extract of red quinoa with an ethanol/water mixture to obtain a mixture of red quinoa/ethanol/water (110); and separating betanin from the mixture of red quinoa/ethanol/water by supercritical fluid fractionation, which operated under a pressure between 2300 to 4400 psi at a temperature between 35 to 65° C. for a period of time between 15 to 90 minutes (120).

In step (110), the ratio of the ethanol/water mixture ranged from 60:40 to 80:20, more preferably, the ratio of the ethanol/water mixture ranged from 60:40 to 70:30, and most preferably, the ratio of the ethanol/water mixture was 70:30. Further, the extract of red quinoa mentioned in the specification was the red quinoa extract that contained at least 2000 ppm of betanin.

In step (120), more preferably, the pressure was between 2300 to 3700 psi, and most preferably, the pressure was 3700 psi. More preferably, the temperature was between 35 to 55° C., and most preferably, the temperature was 35° C. More preferably, the period of time was between 30 to 90 minutes, and most preferably, the period of time was 30 minutes. It was of particular note that some of the operation parameters might be fine-tuned as necessary. Those skilled in the art might obtain the optimal parameters through experiments. It was not necessary to specify certain parameters for achieving the effect of the present invention within the scope of the operation conditions disclosed by the present invention.

In the present invention, the optimal combination of operation conditions was found by using "Taguchi" method. The so-called "Taguchi" method belongs to quality engineering, which manages and controls the processes of experiment and production by way of statistics, in order to improve the quality and reduce the cost of products. The present invention primarily used Taguchi method to find the most efficient conditions of operating environment.

According to the experiment operations, using the method of separating betanin from red quinoa by supercritical fluid fractionation of the present invention, the content of betanin in the extract of red quinoa was increased from 2400 ppm to 3200 ppm, which equaled to a 33% increase.

Therefore, with reference to the accompanying drawing, the present invention had the following advantages over the conventional technique: the method of separating betanin from red quinoa by supercritical fluid fractionation of the present invention increased the content of betanin in the extract of red quinoa effectively.

However, the description above illustrates preferred embodiments of the present invention only and doesn't intend to limit the scope of the present invention. Therefore, all the simple modifications and equivalent structural changes made by using the content of the specification and the drawing of the present invention are encompassed within the claim scope of the invention.

What is claimed is:

1. A method of separating betanin from red quinoa by supercritical fluid fractionation, including:
    mixing an extract of red quinoa with an ethanol/water mixture to obtain a mixture of red quinoa/ethanol/water; and
    separating betanin from the mixture of red quinoa/ethanol/water by supercritical fluid fractionation, which operates under a pressure between 2300 to 4400 psi at a temperature between 35° C. to 65° C. for a period of time between 15 to 90 minutes,
    wherein the extract of red quinoa contains at least 2000 ppm of betanin; the ratio of the ethanol/water mixture ranges from 60:40 (inclusive) to 70:30 (exclusive).

2. The method of claim 1, wherein the pressure is between 2300 to 3700 psi.

3. The method of claim 2, wherein the pressure is 3700 psi.

4. The method of claim 1, wherein the temperature is between 35 to 55° C.

5. The method of claim 4, wherein the temperature is 35° C.

6. The method of claim 1, wherein the period of time is between 30 to 90 minutes.

7. The method of claim 5, wherein the period of time is 30 minutes.

\* \* \* \* \*